US00PP19514P2

(12) United States Plant Patent
Verschoor

(10) Patent No.: US PP19,514 P2
(45) Date of Patent: Dec. 2, 2008

(54) ***PHLOX* PLANT NAMED 'PURPLE KISS'**

(50) Latin Name: ***Phlox paniculata* hybid**
Varietal Denomination: Purple Kiss

(75) Inventor: Jan Verschoor, Haarlem (NL)

(73) Assignee: Witteman & Co., Hillegom (NL)

( * ) Notice: Subject to any disclaimer, the term of this patent is extended or adjusted under 35 U.S.C. 154(b) by 0 days.

(21) Appl. No.: 11/986,869

(22) Filed: Nov. 27, 2007

(51) Int. Cl.
*A01H 5/00* (2006.01)

(52) U.S. Cl. ..... Plt./320

(58) Field of Classification Search ..... Plt./320
See application file for complete search history.

*Primary Examiner*—Annette H Para
*Assistant Examiner*—S. B. McCormick-Ewoldt
(74) *Attorney, Agent, or Firm*—Jondle & Associates, P.C.

(57) ABSTRACT

A new *phlox* plant particularly distinguished by intense deep purple petals with a pure white eye, compact plant habit, healthy foliage and good mildew resistance, is disclosed.

2 Drawing Sheets

Genus and species: *Phlox paniculata* hybid.
Variety denomination: 'Purple Kiss'.

BACKGROUND OF THE NEW PLANT

The present invention comprises a new and distinct cultivar of *phlox*, botanically known as *Phlox paniculata,* and hereinafter referred to by the cultivar name 'Purple Kiss'. The new cultivar originated from an open pollination in 2005 in Haarlem, The Netherlands between unknown male and female *Phlox paniculata* plants.

The new cultivar was selected from the results of the open pollination in 2006 in Haarlem. The Netherlands and has been asexually reproduced through two generations by vegetative cuttings in Haarlem, The Netherlands since that time. The present invention has been found to retain its distinctive characteristics through successive asexual propagations.

SUMMARY OF THE INVENTION

The following are the most outstanding and distinguishing characteristics of this new cultivar when grown under normal horticultural practices in Haarlem, The Netherlands.

1. Intense deep purple petals with pure white eye;
2. Florets up to 4 cm in diameter;
3. Compact habit;
4. Healthy foliage; and
5. Good mildew resistance.

DESCRIPTION OF PHOTOGRAPHS

This new *phlox* plant is illustrated by the accompanying photographs which show blooms and foliage of the plant in full color, the colors shown being as true as can be reasonably obtained by conventional photographic procedures. The photographs are of a 4-month-old plant grown in a greenhouse in Haarlem, The Netherlands.

DESCRIPTION OF THE NEW CULTIVAR

Figure 1:
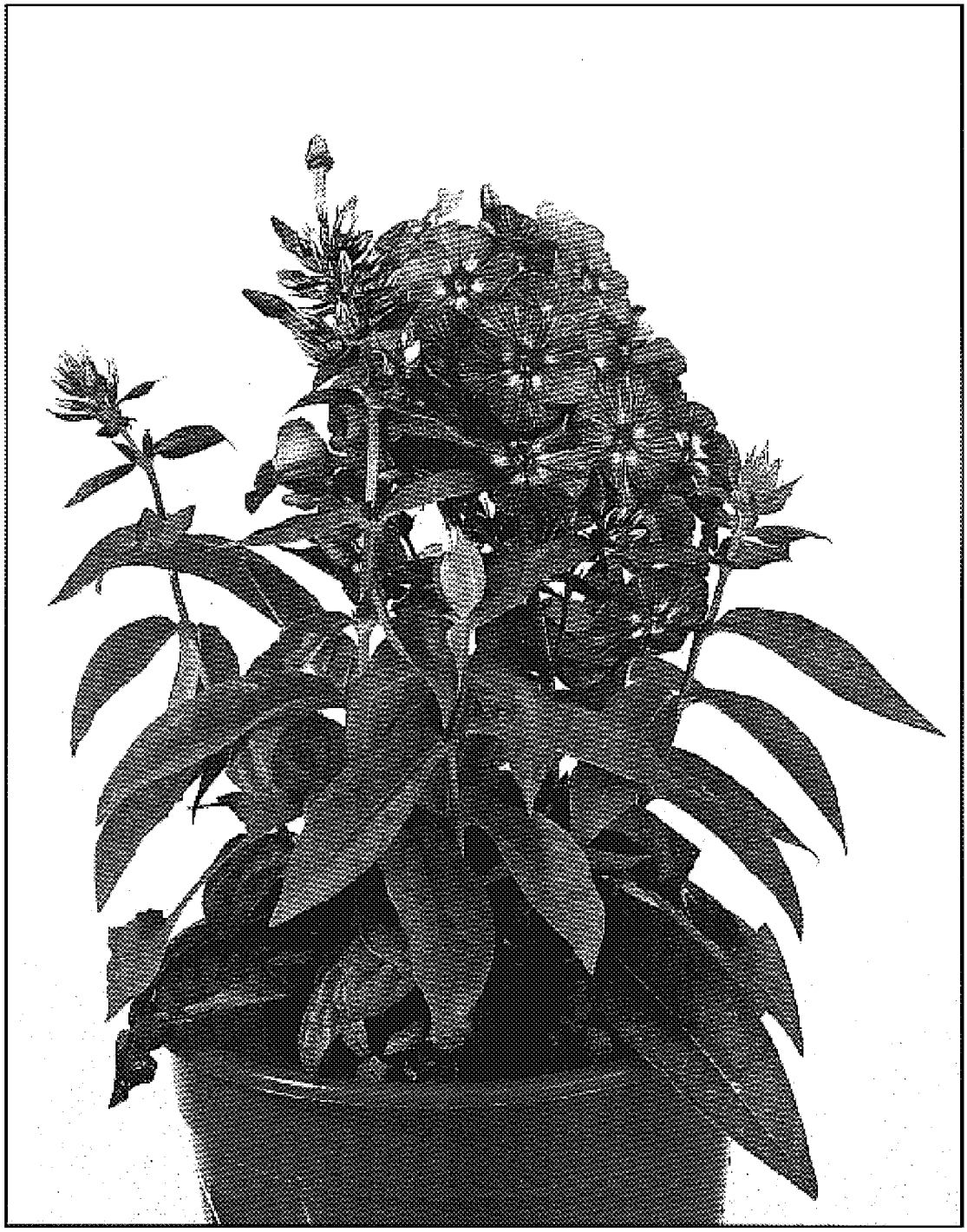
FIG. 1 shows the overall plant habit, including blooms, buds and foliage.
Figure 2:
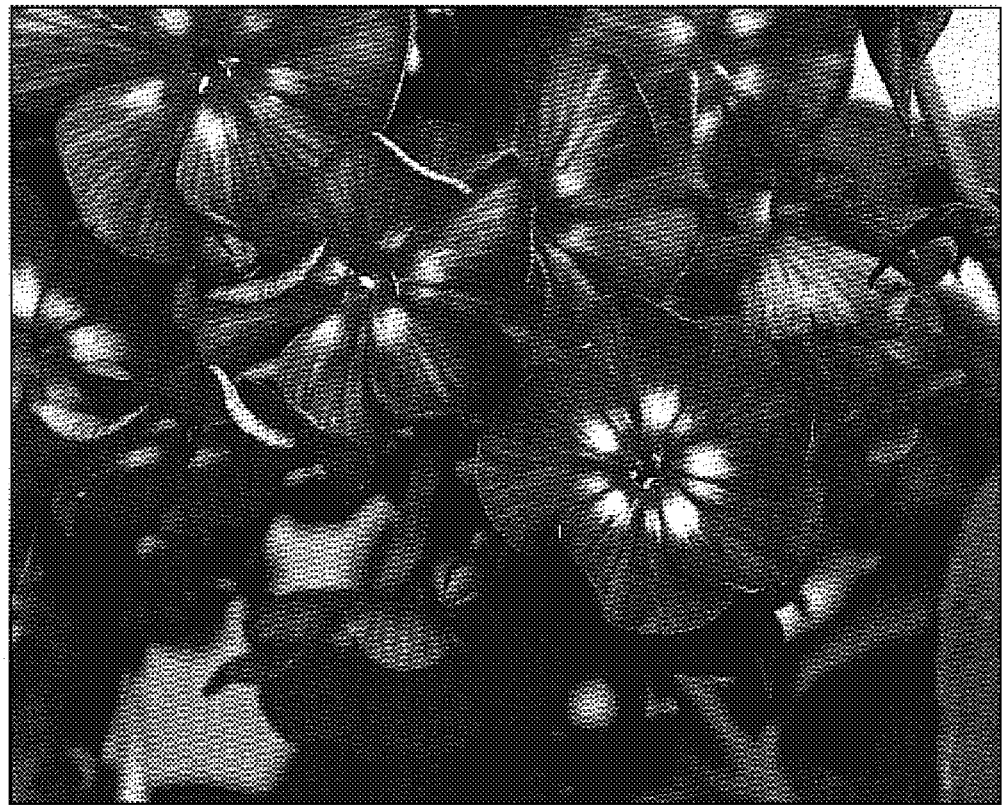
FIG. 2 shows mature flowers.
Figure 3:
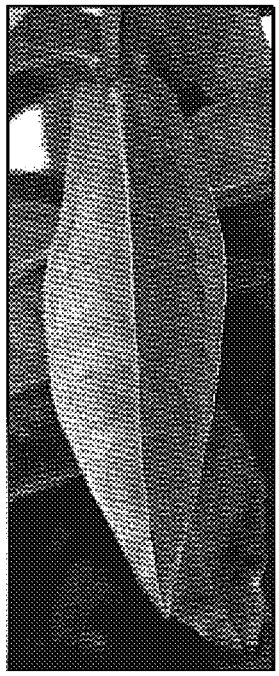
FIG. 3 shows a mature leaf of the plant.

The following detailed description sets forth the distinctive characteristics of 'Purple Kiss'. The data which define these characteristics were collected from asexual reproductions carried out in Haarlem, The Netherlands. The plant history was taken in August on 2-year-old plants which were planted and grown outdoors in daytime temperatures between 14° C. and 32° C. and nighttime temperatures between 5° C. and 15° C. No pinchings, growth retardants or photoperiodic treatments were used. Observations were made when the plants were in natural outdoor light. Color references are primarily to the R.H.S. Colour Chart of The Royal Horticultural Society of London (R.H.S.) (2001).

DETAILED BOTANICAL DESCRIPTION

Classification:
- *Family.*—Polemoniaceae.
- *Botanical.*—*Phlox paniculata.*
- *Common name.*—*Phlox.*

Parentage:
- *Female parent.*—Unknown.
- *Male parent.*—Unknown.

Growth:
- *Form.*—Herbaceous perennial.
- *Habit.*—Upright, moderate to low vigor.
- *Shape.*—Inverted triangle.
- *Height* (*measured from the top of the soil*).—30.8 cm.
- *Diameter.*—22.6 cm.
- *Growth rate.*—10 cm per month.
- *Flowering response.*—60 days.
- *Time to produce a finished flowering plant.*—25 weeks from rooted cutting for a 1.5 liter container.
- *Time to initiate and develop roots during summer.*—30 days.
- *High temperature tolerance.*—Tolerant to at least 35° C.
- *Lower temperature tolerance.*—Hardy to USDA Zone 4.
- *Roots.*—White, thin, fibrous, sparse, freely branching.

Branches:
- *Habit.*—Moderate basal branching.
- *Number of branches.*—1 flowering stem.

*Stems:*
*Description.*—Round, glabrous, slightly glossy.
*Aspect.*—Rounded.
*Color.*—RHS 144A (Yellow-green).
*Diameter.*—0.4 cm.
*Stem length* (*excluding inflorescence*).—16.0 cm.
*Internode length.*—2.5 cm.
*Strength.*—Strong.
*Pubescence.*—Absent.

Leaves:
*Arrangement.*—Opposite, single.
*Quantity of leaves* (*per lateral branch*).—14.
*Durability to stress.*—High.
*Shape.*—Elliptic.
*Apex.*—Apiculate.
*Base.*—Truncate to obtuse.
*Color* (*mature leaves*).—Upper surface: RHS 137A (Green) to RHS 137B (Green). Lower surface: RHS 138B (Green).
*Color* (*immature leaves*).—Upper surface: RHS 143A (Green), heavily tinged with RHS N186A (Greyed-purple). Lower surface: RHS 143C (Green) to RHS 143D (Green) tinged with RHS N186A (Greyed purple) to RHS 186B (Greyed purple).
*Margin.*—Revolute, short, finely serrate (approx. 30 teeth per cm).
*Size.*—Length: 10.2 cm. Width: 3.4 cm.
*Texture.*—Smooth, glabrous.
*Pubescence.*—Absent.
*Venation.*—Type: Pinnate. Color: Upper surface: RHS 145A (Yellow-green). Lower surface: RHS 145B (Yellow-green) to RHS 145C (Yellow-green).
*Petiole.*—Shape: V-shaped. Length: 0.3 cm. Diameter: 0.4 cm. Color (Both surface): RHS 145B (Yellow-green) to RHS 145C (Yellow-green).

Flower buds:
*Color.*—RHS 83D (Violet); lower half (immature calyx) RHS 145A (Yellow-green); flushed with RHS N186C (Greyed-purple).
*Shape.*—Elliptic.
*Size.*—Length: 1.8 cm. Diameter: 0.5 cm.
*Rate of opening.*—Open approximately 4 days from stage described above.

Inflorescence:
*Blooming habit.*—Continuous once a year.
*Inflorescence type.*—Self-cleaning, compound terminal panicle.
*Natural flowering season.*—Summer to late summer (July to September).
*Height.*—13.0 cm.
*Width.*—12.4 cm.
*Fragrance.*—Moderate, sweet; typical *Phlox paniculata* scent.
*Flower number* (*per inflorescence*).—75.
*Quantity of flowers per lateral stem.*—25.
*Quantity of flower buds per lateral stem.*—50.
*Quantity of flower and buds per plant.*—75.
*Rate of flower opening.*—Approximately 30% of the flowers at any stage.
*Flower longevity on plant.*—10 days.
*Flower longevity as a cut flower.*—10 days.

Peduncle:
*Color.*—RHS 144A (Yellow-green) to RHS 144B (Yellow-green).
*Length.*—Primary: 9.9 cm. Secondary: 2.8 cm.
*Diameter.*—Primary: 0.3 cm. Secondary: 0.15 cm.
*Angle.*—Primary peduncles average angle 0° (straight upright), secondary peduncles with an average angle of 40°.
*Strength.*—Strong.

Pedicel:
*Color.*—RHS 144A (Yellow-green) to RHS 144B (Yellow-green).
*Length.*—0.5 cm.
*Diameter.*—0.1 cm.
*Angle.*—Average angle 30° (0° to 60°) (0°=straight on top of the peduncle).
*Strength.*—Strong.

Florets:
*Type.*—Single.
*Shape.*—Salverform.
*Aspect.*—Upright to outward.
*Fragrance.*—Moderate, sweet; typical *Phlox paniculata* scent.
*Size.*—Height (flower depth): 3.0 cm. Diameter: 3.5 cm.
*Petals.*—Arrangement: Rotate. Shape: Spathulate, the lower 60% fused into a tube. Appearance: Dull, smooth. Number: 5, fused into a tube (lower 60% of each petal). Size: Length: 4.3 cm (lower 2.5 cm fused into a tube). Width: 2.1 cm. Apex: Rounded. Margin: Entire. Color (when opening): Upper surface: RHS N81A (Purple-violet), base of free part spotted RHS N155A (White), tube RHS 70C (Red-purple). Lower surface: RHS N82B (Purple-violet) to RHS N82C (Purple-violet), tube RHS 186A (Greyed-purple) to RHS 186B (Greyed-purple). Color (fully opened): Upper surface: RHS N82C (Purple-violet) to RHS N82D (Purple-violate), veins RHS N82A (Red), base of free part spotted RHS N155A (White), tube RHS 76C (Purple). Lower surface: RHS 85B (Violet) to RHS 85C (Violet), veined RHS 86C (Darker violet), tube RHS 76C (Purple). Color fading to: RHS N82C (Purple-violet), veins RHS N82B to RHS N82C (Darker violet). Texture (both surfaces): Smooth.

Calyx:
*Shape.*—Campanulate.
*Length.*—1.1 cm.
*Diameter.*—0.5 cm.
*Sepals.*—Arrangement: Rotate. Appearance: Smooth, dull. Number: 5. Shape: Linear. Apex: Narrow apiculate. Base: Lower 55% fused. Margin: Entire. Size: Length: 1.1 cm. Width: 0.2 cm. Color (mature): RHS 145A (Yellow-green); flushed with RHS N186C (Greyed-purple) to RHS 202A (Black). Color (immature-both surfaces): RHS 145A (Yellow-green); flushed with RHS N186C (Greyed-purple).

Reproductive organs:
*Stamens.*—Quantity: 5. Anther: Shape: Basifixed, oblong; filament implanted in petal. Length: 0.3 cm. Length of filament: 0.1 cm. Color: RHS 4C (Yellow) to RHS 4D (Yellow).
*Pollen.*—Amount: Moderate. Color: RSH 11D (Yellow).
*Pistil.*—Quantity: 1. Length: 2.4 cm.
*Style.*—Length: 2.3 cm. Color: RHS 150D (Yellow-green).
*Stigma.*—Shape: Cleft (3-parted). Color: RHS 145C (Yellow-green) to RHS 145D (Yellow-green).
*Ovary color.*—RHS 143A (Green).

Fruit and seed set: No fruit or seeds have been detected to date.

Disease and insect resistance: No particular resistance or susceptibility to diseases or insects noted to date.

COMPARISON WITH PARENTAL AND COMMERCIAL CULTIVARS

'Purple Kiss' differs from the commercial *Phlox paniculata* variety 'Wilhelm Kesselring' (unpatented), by having healthier foliage with thicker stems and a sturdier plant habit than 'Wilhelm Kesselring'. Additionally, 'Purple Kiss' has a more compact plant habit and flowers that are larger and have a richer color than 'Wilhelm Kesselring'.

'Purple Kiss' differs from the commercial *Phlox* variety 'Grenadine Dream' (U.S. Plant patent application Ser. No. 11/725,797), by having intense purple petals with a pure white eye while 'Grenadine Dream' has rich red-purple flowers.

I claim:

1. A new and distinct cultivar of *phlox* plant as shown and described herein.

* * * * *